United States Patent
Okubo

(10) Patent No.: US 10,617,377 B2
(45) Date of Patent: Apr. 14, 2020

(54) X-RAY IMAGE CAPTURING DEVICE

(71) Applicant: Shimadzu Corporation, Kyoto (JP)

(72) Inventor: Shohei Okubo, Kyoto (JP)

(73) Assignee: Shimadzu Corporation, Nakagyo-ku, Kyoto-shi, Kyoto (JP)

(*) Notice: Subject to any disclaimer, the term of this patent is extended or adjusted under 35 U.S.C. 154(b) by 172 days.

(21) Appl. No.: 15/871,343

(22) Filed: Jan. 15, 2018

(65) Prior Publication Data

US 2018/0214103 A1 Aug. 2, 2018

(30) Foreign Application Priority Data

Jan. 30, 2017 (JP) .................. 2017-014454

(51) Int. Cl.
*A61B 6/00* (2006.01)
*A61B 6/03* (2006.01)
*A61B 6/04* (2006.01)
*A61B 6/06* (2006.01)

(52) U.S. Cl.
CPC ............ *A61B 6/463* (2013.01); *A61B 6/0407* (2013.01); *A61B 6/0457* (2013.01); *A61B 6/06* (2013.01); *A61B 6/481* (2013.01); *A61B 6/504* (2013.01); *A61B 6/5241* (2013.01); *A61B 6/589* (2013.01); *A61B 6/487* (2013.01)

(58) Field of Classification Search
CPC ......... A61B 6/4441; A61B 6/03; A61B 6/504; A61B 5/1114; A61B 5/742; A61B 6/032; A61B 6/037; A61B 6/04; A61B 8/08; A61B 5/0037; A61B 5/1128; A61B 90/39
See application file for complete search history.

(56) References Cited

U.S. PATENT DOCUMENTS

2017/0340299 A1* 11/2017 Grass .................. A61B 6/03

FOREIGN PATENT DOCUMENTS

| JP | 2005046444 A | 2/2005 |
|---|---|---|
| JP | 2007222500 A | 9/2007 |
| JP | 2008148982 A | 7/2008 |
| JP | 2009-254570 | 11/2009 |
| JP | 2011062433 A | 3/2011 |
| JP | 2011-072521 | 4/2011 |
| JP | 2016190016 A | 11/2016 |

OTHER PUBLICATIONS

Notice of Reasons for Refusal, dated Nov. 19, 2019, from the Japanese Patent Office for corresponding Japanese Patent Application No. 2017-014454, and English-language machine translation thereof (7 pages total).

* cited by examiner

*Primary Examiner* — Don K Wong
(74) *Attorney, Agent, or Firm* — Muir Patent Law, PLLC

(57) ABSTRACT

The X-ray image capturing device includes a top board for laying a subject thereon, an image capturing unit for capturing an X-ray image, an image processing unit for generating an elongate image which is an image longer than the X-ray image by performing joining processing of a plurality of X-ray images, and a display unit for displaying an elongate image. Based on the position information on the top board and the image capturing unit, the image capturing range of the image capturing unit is displayed on the elongate image.

18 Claims, 10 Drawing Sheets

Top board movement image capturing

[First Embodiment]

Current image capturing rang is displayed on elongate image

[Second Embodiment]

[Third Embodiment]

[Fourth Embodiment]

[Fifth Embodiment]

X-RAY IMAGE CAPTURING DEVICE

CROSS-REFERENCE TO RELATED APPLICATIONS

The present application claims priority to Japanese Patent Application No. 2017-014454, entitled "X-ray image capturing device", filed on Jan. 30, 2017, and invented by Shohei Okubo, the contents of which are incorporated by reference in their entirety.

BACKGROUND OF THE INVENTION

Field of the Invention

The present invention relates to an X-ray image capturing device.

Description of Background Art

Conventionally, an X-ray image capturing device is known in which an X-ray transmitted through a subject is detected to image an inside of the subject. Such an X-ray image capturing device is disclosed in, for example, Japanese Unexamined Patent Application Publication No. 2009-254570.

The aforementioned Japanese Unexamined Patent Application Publication No. 2009-254570 discloses an X-ray image capturing device. The X-ray image capturing device is equipped with a top board for laying a subject thereon, an X-ray tube for irradiating the subject with an X-ray, an X-ray detector for detecting the transmitted X-ray from the subject, a support unit for supporting the X-ray tube and the X-ray detector so that the X-ray tube and the X-ray face with each other across the top board, a moving mechanism for relatively moving the support unit and the top board, an image capturing unit for capturing an X-ray transparent image by detecting the transmitted X-ray with the X-ray detector, and an X-ray transparent image output unit for outputting the X-ray transparent image.

The X-ray image capturing device disclosed by the Japanese Unexamined Patent Application Publication No. 2009-254570 is configured as follows. The moving mechanism is controlled so as to relatively move the support unit and the top board so that the X-ray tube and the X-ray detector are moved in the longitudinal direction of the subject. During the movement, an X-ray is sequentially irradiated to the subject from the X-ray tube. Each time, the transmitted X-ray from the subject is detected by the X-ray detector to capture the X-ray transparent image (top board movement image capturing).

The X-ray image capturing device disclosed in Japanese Unexamined Patent Application Publication No. 2009-254570 can generate an elongate image longer than a single X-ray image by performing joining processing of the X-ray images acquired by the "top board movement image capturing" based on the image capturing position information on the respective X-ray images. Therefore, the X-ray image capturing device of the aforementioned Patent Document 1 is particularly utilized for surgery, etc., which requires a large movement of the image capturing range because it cannot be fit in a single X-ray image as in a lower limb operation.

However, in the X-ray image capturing device as disclosed in Japanese Unexamined Patent Application Publication No. 2009-254570, when moving the image capturing range of the image capturing unit to the position where the operator performs surgery, it is necessary to perform X-ray fluoroscopy to grasp the current image capturing range. Especially, when the movement distance of the image capturing range becomes larger like a lower limb, the time to perform the X-ray fluoroscopy becomes longer correspondingly. Then, in proportion to the time of the X-ray fluoroscopy, the X-ray dose exposing the subject increases. As described above, in the X-ray image capturing device as disclosed in the aforementioned Patent Document 1, in cases where the image capturing range must be moved largely because it cannot be fitted in a single X-ray image, there is a problem that the subject's X-ray exposure dose increases since the X-ray fluoroscopy must be performed during the movement period in which the operator moves the image capturing range to a target position. Incidentally, the "X-ray fluoroscopy" is an image capturing method in which the X-ray dose is relatively reduced as compared with the "X-ray image capturing", and is temporarily used (not saved).

SUMMARY OF THE INVENTION

The present invention was made to solve the aforementioned problems. One object of the present invention is to provide an X-ray image capturing device capable of reducing a subject's X-ray exposure dose even when an image capturing range for a subject has to be largely moved.

In order to achieve the aforementioned object, an X-ray image capturing device according to one aspect of the present invention includes a top board configured to lay a subject thereon, an image capturing unit configured to capture an X-ray image by irradiating the subject with the X-ray and detecting the X-ray transmitted through the subject, an image processing unit configured to generate an elongate image which is an image longer than the X-ray image by performing joining processing of a plurality of the X-ray images, and a display unit configured to display the elongate image. An image capturing range of the image capturing unit is displayed on the elongate image based on position information on the top board and the image capturing unit.

In the X-ray image capturing device according to one aspect of the present invention, as described above, it is configured such that the image capturing range of the image capturing unit is displayed on the elongate image based on the position information on the top board and the image capturing unit. With this, the current image capturing range can be grasped on a pre-generated elongate image. Therefore, an operator can move the top board and the image capturing unit so that the image capturing range on the elongate image is located at a target image capturing position without requiring additional X-ray fluoroscopy during the movement period in which the operator moves the image capturing range to a target position. As a result, even in cases where the image capturing range with respect to the subject needs to be moved greatly, the subject's X-ray exposure dose can be reduced.

In the X-ray image capturing device according to the aforementioned one aspect of the present invention, it is preferably configured such that the X-ray image capturing device further includes a moving mechanism capable of changing a relative position of the top board with respect to the image capturing unit and a position information acquisition unit configured to acquire the position information and that the image capturing range is displayed on the elongate image based on a change in the position information due to a change in the relative position by the moving mechanism. With this configuration, the image capturing range on the elongate image changes based on the change in the position of the top board and the image capturing unit moved by the moving mechanism. Therefore, even in cases where the relative position is changed by the moving mechanism, the image capturing range can be changed according to the change in the relative position. As a result, an operator can assuredly grasp the position of the current image capturing range by confirming the image capturing range displayed on the display unit. For this reason, it becomes possible to easily move the top board and the image capturing unit so that the image capturing range on the elongate image is positioned on a target image capturing position.

In the X-ray image capturing device according to the aforementioned one aspect of the present invention, it is preferably configured such that the elongate image is generated by performing joining processing of the X-ray images based on image capturing position information which is the position information at the time of capturing the X-ray image and the image capturing range based on current position information is displayed on the elongate image generated based on the image capturing position information. With this configuration, the image capturing position information for generating the elongate image and the current position information for displaying the current image capturing range both become the position information on the top board and the image capturing unit. For this reason, by associating the image capturing position information with the current position information, an accurate image capturing range can be displayed on the elongate image.

In the X-ray image capturing device according to the aforementioned one aspect of the present invention, it is preferably configured such that a size or a shape of the image capturing range to be displayed on the elongate image is adjusted based on a change in the position information. With this configuration, when the size or the shape of the image capturing range is changed according to the change in the position of the top board and the image capturing unit and the image capturing condition of the image capturing unit on the elongate image, the changed image capturing range can be displayed on the display unit. For this reason, it becomes possible to assuredly make an operator recognize the size or the shape of the image capturing range to be actually acquired.

In the configuration in which the size or the shape of the image capturing range is adjusted, it is preferably configured such that the image capturing unit includes an X-ray irradiation unit configured to irradiate the subject with the X-ray and an X-ray detection unit configured to detect the X-ray transmitted through the subject, the X-ray irradiation unit and the X-ray detection unit are configured to be changed in a distance therebetween, and that a size of the image capturing range to be displayed on the elongate image is adjusted based on the change in the position information due to a change in a distance between the X-ray irradiation unit and the X-ray detection unit. With this configuration, it becomes possible to display an image capturing range reflecting the change in the distance between the X-ray irradiation unit and the X-ray detection unit on the elongate image. As a result, an operator can easily enlarge or reduce the image capturing range to be displayed on the elongate image by adjusting the distance between the X-ray irradiation unit and the X-ray detection unit to set the image capturing range to a predetermined size.

In the configuration in which the size or the shape of the image capturing range is adjusted, it is preferably configured such that the top board is adjustable in a height position and the image capturing range to be displayed on the elongate image is adjustable in a size based on a change in the position information due to a change in the height position of the top board. With this configuration, it is possible to display an image capturing range reflecting the change in the height position of the top board on the elongate image. As a result, an operator can easily enlarge or reduce the image capturing range to be displayed on the elongate image by adjusting the height position of the top board to set the image capturing range to a predetermined size.

In the configuration in which the size or the shape of the image capturing range can be adjusted, it is preferably configured such that the top board and the image capturing unit are adjustable in an angle therebetween and the image capturing range to be displayed on the elongate image is adjusted in shape based on the change in the position information due to a change of an angle formed by the top board and the image capturing unit. With this configuration, it is possible to display the image capturing range reflecting the change in the angle formed by the top board and the image capturing unit on the elongate image. As a result, an operator can make the image capturing range to be displayed so as to correspond to various angles on the elongate image by adjusting the angle between the top board and the image capturing unit.

In the X-ray image capturing device according to the aforementioned one aspect of the present invention, it is preferably configured such that the image capturing unit includes an X-ray irradiation field adjusting unit capable of changing an X-ray radiation field which is an irradiation range of an X-ray and the image capturing range to be displayed on the elongate image is adjustable in size based on a change of the X-ray radiation field. With this configuration, it is possible to display the image capturing range reflecting the change of the X-ray radiation field on the elongate image. As a result, an operator can easily enlarge or reduce the image capturing range to be displayed on the elongate image by adjusting the X-ray radiation field and also can move the top board and the image capturing unit to a target position. Further, when the image capturing range is reduced by adjusting the X-ray radiation field, the irradiation range of the X-ray is reduced. Therefore, the subject's X-ray exposure dose can be reduced at the time of the X-ray fluoroscopy or the X-ray image capturing at the target position.

In the X-ray image capturing device according to the aforementioned one aspect of the present invention, it is preferably configured such that the X-ray image and the elongate image include an image in which a lower limb portion of the subject is image-captured. Here, since the elongate image is generally generated when an X-ray image of a lower limb portion of a subject is captured, it is particularly effective that the present invention in which the image capturing range is displayed on the elongate image is applied to an X-ray image capturing device for capturing an image of a lower limb portion of a subject as described above.

DESCRIPTION OF PREFERRED EMBODIMENTS

Hereinafter, embodiments of the present invention will be described with reference to the drawings.
<First Embodiment>
With reference to FIGS. 1A and 1B and FIG. 2, a configuration of an X-ray image capturing device 100 according to a first embodiment of the present invention will be described.
(Configuration of X-ray Image Capturing Device)

Figure 1A:
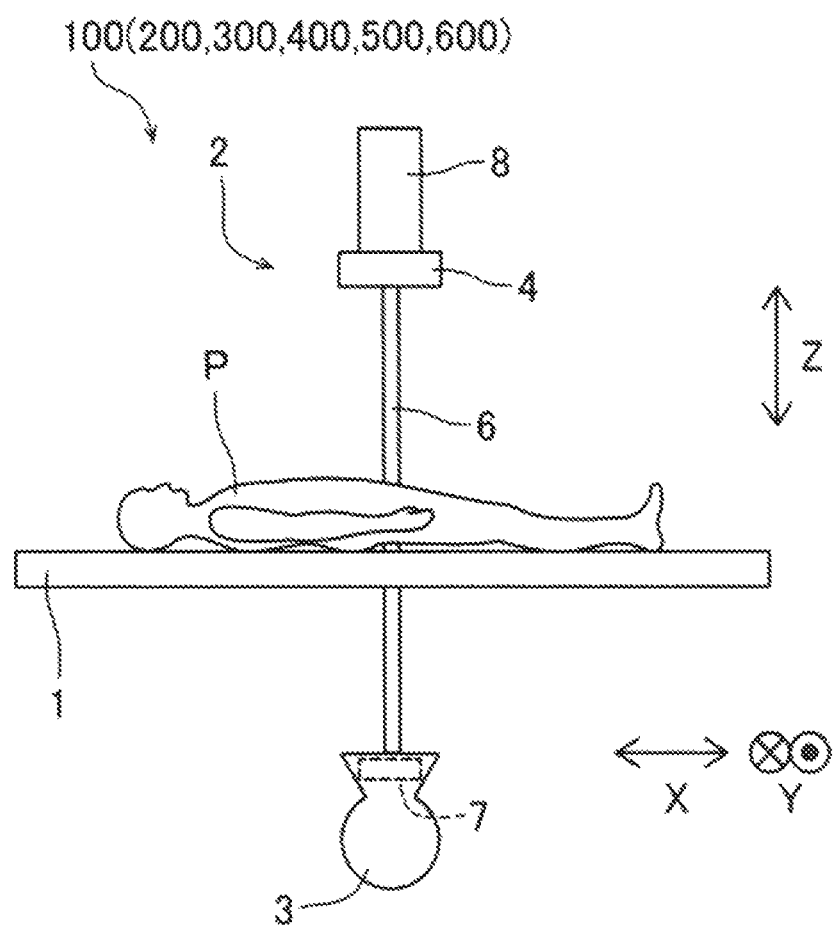
FIG. 1A is a side view and FIG. 1B is a front view showing an overall configuration of an X-ray image capturing device according to a first to sixth embodiments of the present invention.
Figure 1B:
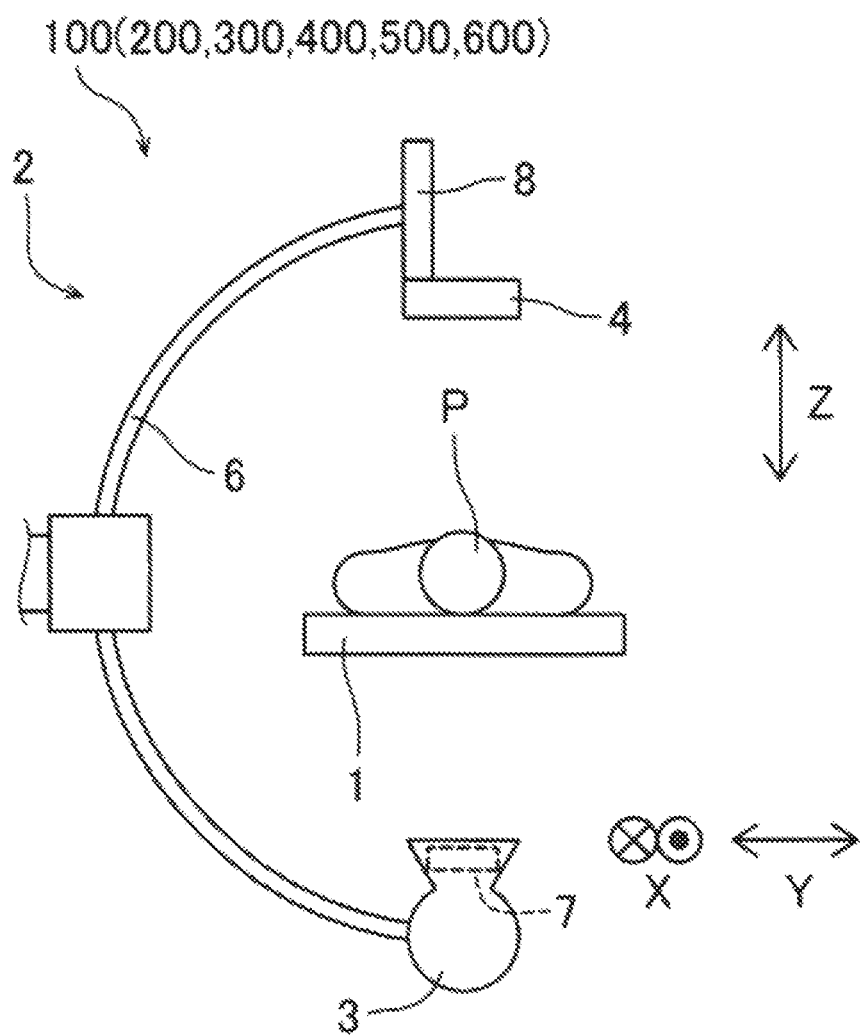

As shown in FIGS. 1A and 1B, the X-ray image capturing device 100 of the first embodiment is equipped with a top board 1 for laying a subject P thereon and an image capturing unit 2 including an X-ray tube device 3 and an X-ray receiver 4. Note that the X-ray tube device 3 is an example of the "X-ray irradiation unit" as recited in claims. Further note that the X-ray receiver 4 is an example of the "X-ray detection unit" as recited in claims.

The top board 1 is formed in a rectangular flat plate shape in plan view. The subject P is laid on the top board 1 so that the head-to-foot direction of the subject P is in parallel to a direction along the long side of the rectangular shape and the left and right direction of the subject P is in parallel to a direction along the short side of the rectangular shape. In this specification, the head-to-foot direction of the subject P is defined as an X direction, the left and right direction of the subject P is defined as a Y direction, and the direction orthogonal to the X direction and the Y direction is defined as a Z direction.

The X-ray tube device 3 is provided with an X-ray source and is arranged on one side of the top board 1. The X-ray tube device 3 is capable of irradiating an X-ray when a voltage is applied by an X-ray tube drive unit (not shown). The X-ray tube device 3 is equipped with a collimator 7 capable of adjusting the X-ray radiation field which is an irradiation range of an X-ray. Further, as shown in FIG. 1B, the X-ray tube device 3 is attached to the one side tip end of a C-shaped arm unit 6. Note that the collimator 7 is an example of the "X-ray irradiation field adjusting unit" as recited in claims.

The X-ray receiver 4 is attached to the other side tip end (the side opposite to the X-ray tube device 3) of the arm unit 6. That is, the X-ray receiver 4 can be arranged on the other side of the top board 1 (on the side opposite to the X-ray tube device 3) with respect to the top board 1. Further, the X-ray receiver 4 includes an FPD (flat panel detector) and is configured to detect X-rays. With this, the X-ray image capturing device 100 is configured so that an X-ray can be irradiated with the X-ray tube device 3 and the X-ray transmitted through the subject P can be detected with the X-ray receiver 4 in a state in which the subject P is laid on the top board 1 so that the X-ray image 21 (see FIG. 4) can be captured. Further, the X-ray receiver 4 is configured so as to be slidable in a direction in which the slide portion 8 extends (in the Z direction in FIGS. 1A and 1B) by the slide portion 8 attached to the tip end of the arm unit 6.

Figure 2:
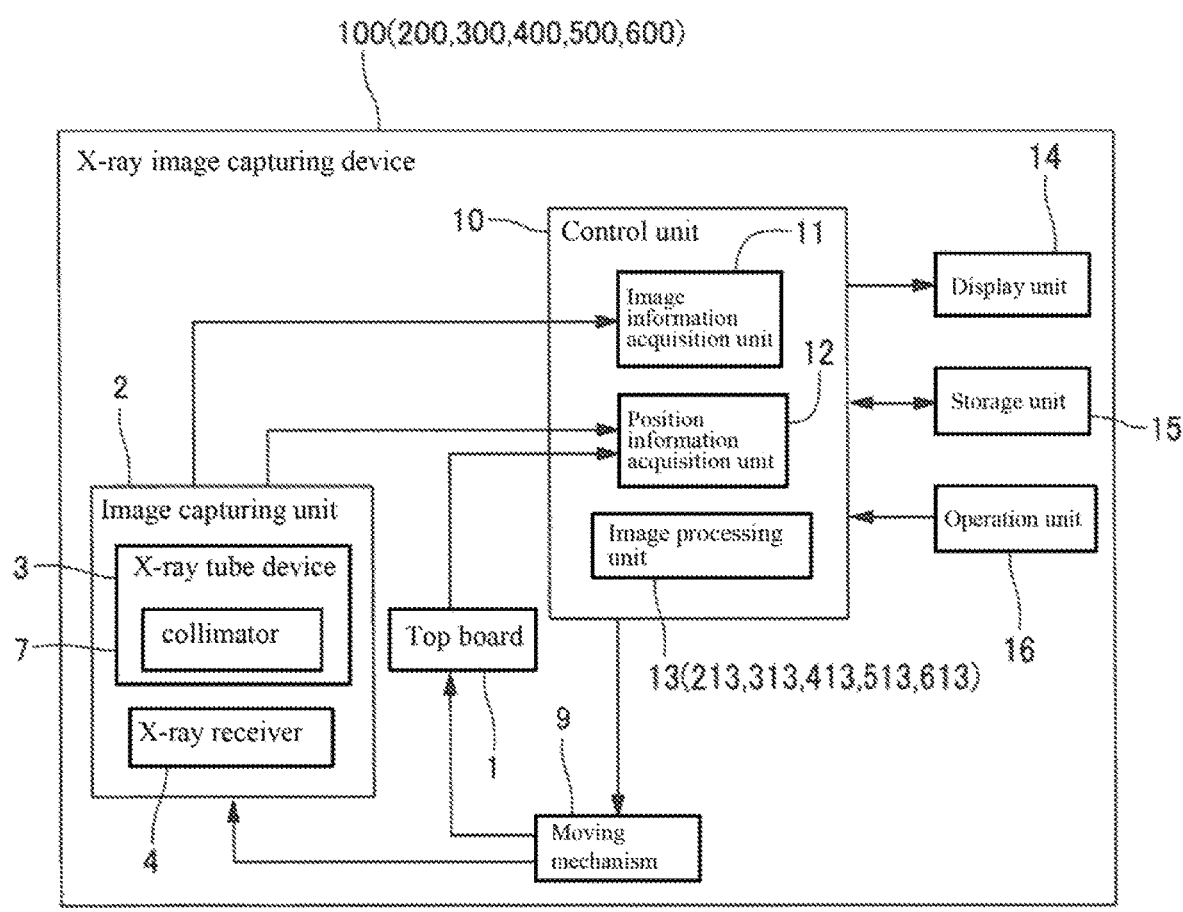
FIG. 2 is a block diagram showing the overall configuration of the X-ray image capturing device.

As shown in FIG. 2, the X-ray image capturing device 100 is further equipped with a moving mechanism 9, a control unit 10, a display unit 14, a storage unit 15, and an operation unit 16.

The moving mechanism 9 is configured so that the top board 1 and the image capturing unit 2 can be moved in an arbitrary direction. That is, by moving either one of or both of the top board 1 and the image capturing unit 2 in any one of the X direction, the Y direction, and the Z direction to change the relative position between the top board 1 and the image capturing unit 2, the position where an image of the subject P is captured (image capturing position 20, see FIGS. 3A and 3B) can be changed. Further, the moving mechanism 9 is configured so that the top board 1 and the arm unit 6 (eventually, the image capturing unit 2) can be rotated on a plane including the X direction and the Z direction (X-Z plane) and on a plane including the Y direction and the Z direction (Y-Z plane). As will be described later, the top board 1 and the image capturing unit 2 are configured so that the angle formed therebetween can be changed. Further, the moving mechanism 9 is configured so that the slide portion 8 can be slid.

The control unit 10 is a computer configured to include a CPU (Central Processing Unit), a ROM (Read Only Memory), a RAM (Random Access Memory), and the like. The control unit 10 is equipped with an image information acquisition unit 11, a position information acquisition unit 12, and an image processing unit 13.

The image information acquisition unit 11 is configured to acquire the image information captured by the image capturing unit 2 from the X-ray receiver 4. The image information acquired by the image information acquisition unit 11 is stored in the storage unit 15 or used for generating an X-ray image 21 by the image processing unit 13.

The position information acquisition unit 12 is configured to acquire the position information on the top board 1 and the image capturing unit 2 moved by the moving mechanism 9. For the position information on the top board 1 and the image capturing unit 2, coordinate information (X, Y, Z) of a plurality of positions is used. Further, the position information on the image capturing unit 2 includes the position information on the X-ray tube device 3 and the X-ray receiver 4. For example, the position information on the top board 1 uses respective coordinate information (X, Y, Z) at positions near the four corners of the top board 1. Further, for the position information on the image capturing unit 2, for example, coordinate information (X, Y, Z) at a total of 4 positions, e.g., any position of the X-ray tube device 3, any position of the X-ray receiver 4, and any two positions of the arm unit 6, is used.

In this way, by using the coordinate information on a plurality of positions on the top board 1 and the image capturing unit 2 as the position information on the top board 1 and the image capturing unit 2, it is possible to specify the positions of the top board 1 and the image capturing unit 2 even in cases where either one of or both of the top board 1 and the image capturing unit 2 is moved in any direction.

Thus, even in cases where the angle formed by the top board 1 and the image capturing unit 2 is changed, the position information acquisition unit 12 can treat as the position information on the top board 1 and the image capturing unit 2 based on a plurality of coordinate information.

The image processing unit 13 is configured to generate an X-ray image 21 based on the image information acquired by the image information acquisition unit 11. Then, the image processing unit 13 is configured such that, based on the position information on the top board 1 and the image capturing unit 2 acquired by the position information acquisition unit 12, an elongate image 22 (see FIG. 4) can be generated by joining X-ray images 21 captured by the image capturing unit 2.

The display unit 14 is configured by, for example, a liquid crystal display. The display unit 14 is configured to display the X-ray image 21 generated by the image processing unit 13 based on the image information captured by the image capturing unit 2 and the elongate image 22 generated by joining X-ray images 21 in the image processing unit 13.

The storage unit 15 includes, for example, a nonvolatile memory. The storage unit 15 stores programs used for the processing of the moving mechanism 9 and the image processing unit 13, and is configured to store the image information captured by the image capturing unit 2 and the position information on the top board 1 and the image capturing unit 2 acquired by the position information acquisition unit 12, or an elongate image 22 generated by the image processing unit 13.

The operation unit 16 includes, for example, a mouse and a keyboard. The operation unit 16 is configured to accept input operations from an operator. The operation unit 16 is configured to transmit the accepted input operation to the control unit 10.

(Generation Method of Elongate Image)

Next, with reference to FIGS. 3A, 3B and 4, a method for generating an elongate image 22 will be described.

Figure 3A:
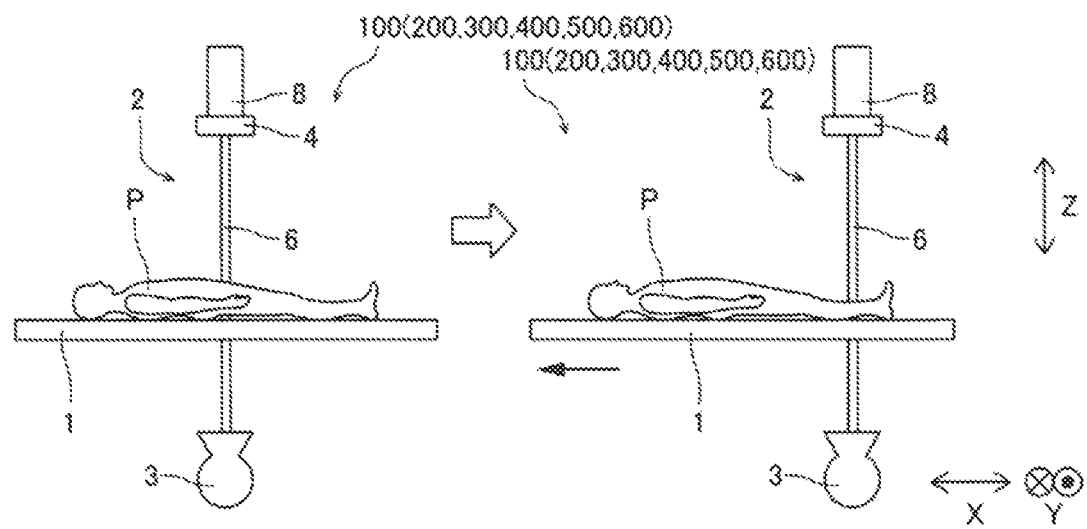
FIGS. 3A and 3B are diagrams for explaining top board movement image capturing.
Figure 3B:
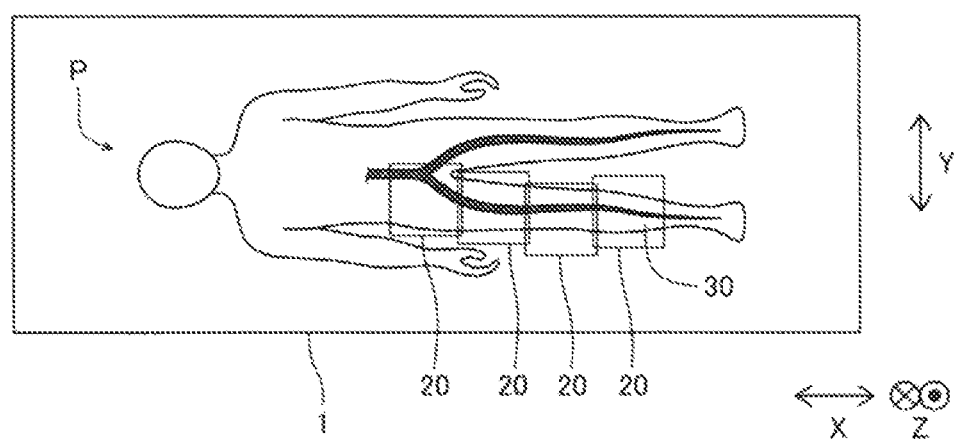

As shown in FIGS. 3A and 3B, in the X-ray image capturing device 100 according to this embodiment, it is configured to perform X-ray image capturing of a plurality of positions of the subject P while moving either one of or both of the top board 1 and the image capturing unit 2 by the moving mechanism 9. FIG. 3B shows an example in which a plurality of positions of a lower limb portion 30 of a subject P is captured by performing X-ray image capturing.

Specifically, as shown in FIG. 3A, by moving the top board 1 in the X direction and the Y direction with respect to the image capturing unit 2, it is possible to perform X-ray image capturing at a plurality of image capturing positions 20 as shown in FIG. 3B. At this time, the image information acquisition unit 11 acquires the X-ray image captured image information, and the position information acquisition unit 12 acquires the position information on the top board 1 and the image capturing unit 2. In the following description, X-ray image capturing at a plurality of image capturing positions 20 by moving the top board 1 in the X direction and the Y direction with respect to the image capturing unit 2 may be sometimes called "top board movement image capturing".

Figure 4:
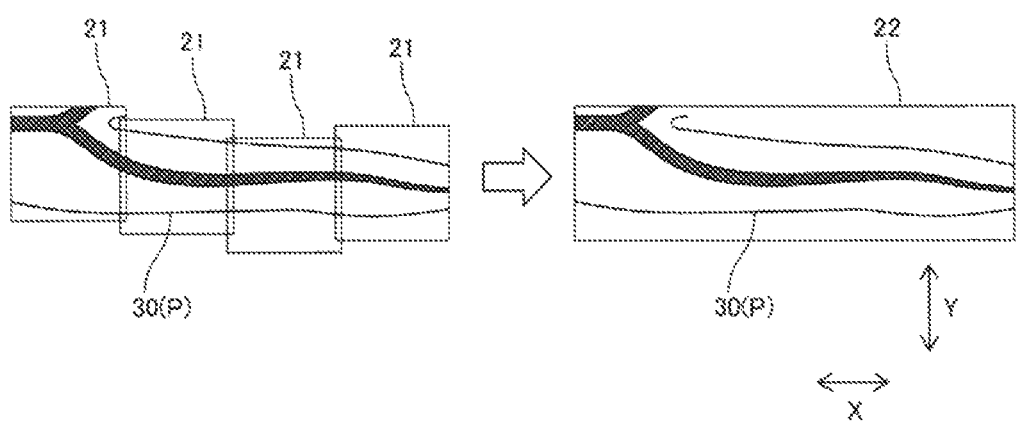
FIG. 4 is a diagram for explaining generation of an elongate image.

As shown in FIG. 4, the image processing unit 13 generates X-ray images 21 obtained by X-ray image capturing at a plurality of image capturing positions 20 from the X-ray image captured image information. The image processing unit 13 generates an elongate image 22 by joining the X-ray images 21 based on the position information on the top board 1 and the image capturing unit 2 at the plurality of image capturing positions 20.

As described above, the elongate image 22 generated by joining X-ray images 21 is associated with the position information on the top board 1 and the image capturing unit 2 at the time of the X-ray image capturing for generating the X-ray images 21 (image capturing position information), and these information is configured to be stored in the storage unit 15.

(Display Method of Current Image Capturing Range on Elongate Image)

Next, with reference to FIGS. 5A and 5B, a method for displaying the current image capturing range 23 on the elongate image 22 will be described. The description will be made assuming that the elongate image 22 has been already generated.

Figure 5A:
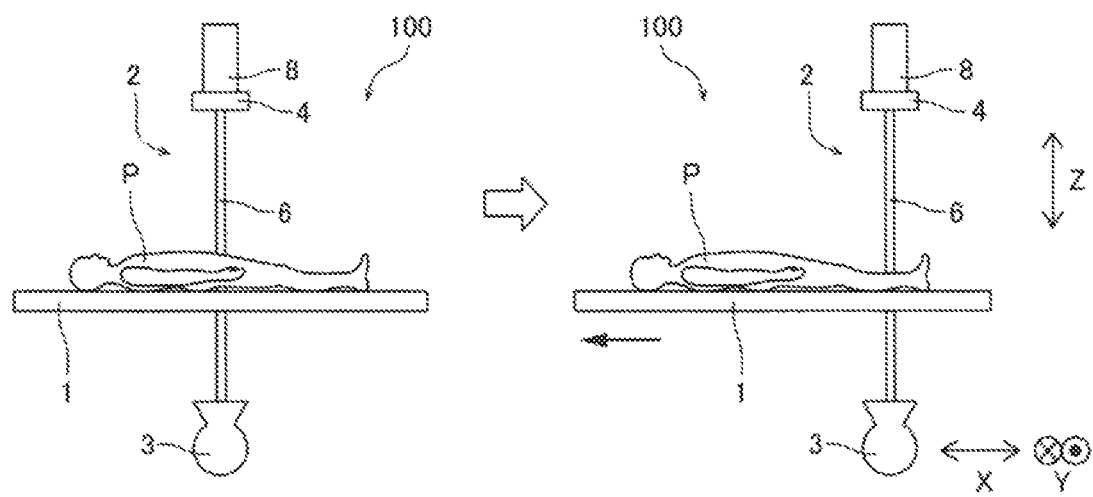
FIGS. 5A and 5B are diagrams for explaining the current image capturing range displayed on the elongate image in the X-ray image capturing device according to the first embodiment.
Figure 5B:
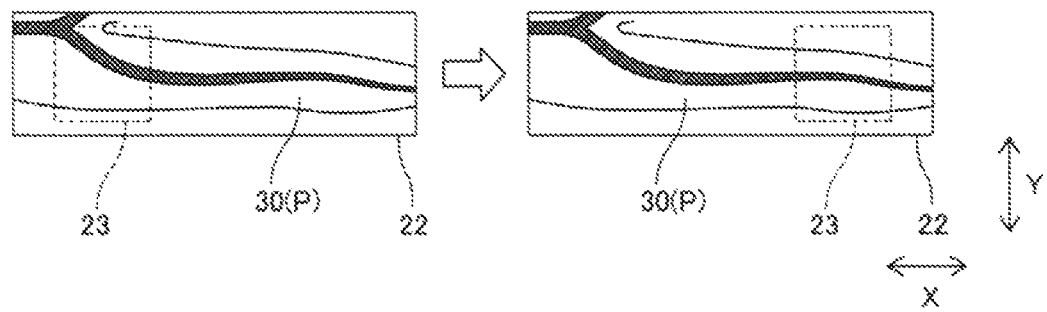

As shown in FIG. 5A, it is possible to move the image capturing range 23 of the current image capturing unit 2 with respect to the subject P by moving either one of or both of the top board 1 and the image capturing unit 2 in the X direction and the Y direction. This image capturing range 23 is a range in which the X-ray irradiated from the X-ray tube device 3 is detected by the X-ray receiver 4. That is, the image capturing range 23 corresponds to a range to be generated as the X-ray image 21 when X-ray image capturing or X-ray fluoroscopy is performed. The X-ray image capturing device 100 according to this embodiment is configured such that the image capturing range 23 can be displayed on the elongate image 22 generated in advance in a superimposed manner.

Specifically, the image processing unit 13 is configured so that the current image capturing range 23 can be superimposed on the elongate image 22 while associating the image capturing position information associated with the elongate image 22 with the position information on the current top board 1 and the image capturing unit 2. That is, in a state in which the current image capturing range 23 is superimposed on the elongate image 22, as shown in FIG. 5A, the relative position of the top board 1 with respect to the image capturing unit 2 is changed by moving either the top board 1 or the image capturing unit 2. In accordance with this, as shown in FIG. 5B, the current image capturing range 23 displayed on the elongate image 22 moves by the amount corresponding to the change of the relative position of the top board 1 with respect to the image capturing unit 2. With this, by generating the elongate image 22 in advance, the operator can assuredly grasp the current image capturing range 23 displayed on the elongate image 22 without separately performing X-ray fluoroscopy.

Further, in the X-ray image capturing device 100 of this embodiment, it is assumed that the position of the subject P with respect to the top board 1 does not substantially change at the time of top board movement image capturing and at the time of displaying the current image capturing range 23 on the elongate image 22 (common condition). As described above, both the image capturing position information used to generate the elongate image 22 and the position information on the current image capturing range 23 are acquired as the position information on the top board 1 and the image capturing unit 2. As described above, the X-ray image capturing device 100 according to the present embodiment is configured so that the current image capturing range 23 can be correctly displayed on the elongate image 22 based on the position information acquired under the common condition.

(Effects of First Embodiment)

In the first embodiment, the following effects can be obtained. In the first embodiment, as described above, it is configured to display the image capturing range 23 of the image capturing unit 2 on the elongate image 22 based on the position information on the top board and the image capturing unit. With this, the current image capturing range 23 can be grasped on the elongate image 22 generated in advance. Therefore, during the movement period during which an operator moves the image capturing range 23 to a target position, even if X-ray fluoroscopy is not performed separately, the operator can move the top board 1 and the image capturing unit 2 so that the image capturing range 23 on the elongate image 22 is located at the target image capturing position. As a result, even in cases where the image capturing range 23 with respect to the subject P has to be largely moved, the X-ray exposure dose of the subject P can be reduced.

Further, in the first embodiment, as described above, the moving mechanism 9 capable of changing the relative position of the top board 1 with respect to the image capturing unit 2 and the position information acquisition unit 12 for acquiring the position information are further provided, and the image capturing range 23 is displayed on the elongate image 22 based on a change in the position information due to a change in the relative position by the moving mechanism 9. With this, the image capturing range 23 on the elongate image 22 changes based on the change in the position of the top board 1 and the image capturing unit 2 moved by the moving mechanism 9. Therefore, even in cases where the relative position is changed by the moving mechanism 9, the image capturing range 23 can be changed according to the change in the relative position. As a result, the operator can assuredly grasp the current position of the image capturing range 23 by confirming the image capturing range 23 displayed on the display unit 14. It becomes easy to move the top board 1 and the image capturing unit 2 so that the image capturing range 23 on the elongate image 22 is located at the target image capturing position.

Further, in the first embodiment, as described above, the elongate image 22 is generated by performing joining processing of the X-ray images 21 based on the image capturing position information which is position information at the time of capturing the X-ray image 21 and the image capturing range 23 based on current position information is displayed on the elongate image 22 generated based on the image capturing position information. With this, the image capturing position information for generating the elongate image 22 and the current position information for displaying the current image capturing range 23 both become the position information on the top board 1 and the image capturing unit 2. By associating the image capturing position information with the current position information, it is possible to display an accurate image capturing range 23 on the elongate image 22.

Further, in the first embodiment, as described above, the X-ray image 21 and the elongate image 22 include an image in which a lower limb portion 30 of the subject P is image-captured. Here, the elongate image 22 is generally generated when the X-ray image capturing is performed on the lower limb portion 30 of the subject P. Therefore, it is particularly effective to apply the present invention for displaying the image capturing range 23 on the elongate image 22 to the X-ray image capturing device 100 for capturing an image of the lower limb portion 30 of the subject P as described above.

<Second Embodiment>

Next, a second embodiment of the present invention will be described with reference to FIGS. 1A, 1B, 2, 6A and 6B. In the second embodiment, an example in which the size of the image capturing range to be displayed on the elongate image 22 is adjusted based on the change in the position information due to the change in the distance between the X-ray tube device 3 and the X-ray receiver 4 will be explained. In the figures, the same reference numeral is given to a part having the same configuration as in the first embodiment.

The X-ray image capturing device 200 according to the second embodiment of the present invention is configured such that the size of the image capturing range 223 to be displayed on the elongate image 22 is changed by changing the distance between the X-ray tube device 3 and the X-ray receiver 4.

Figure 6A:
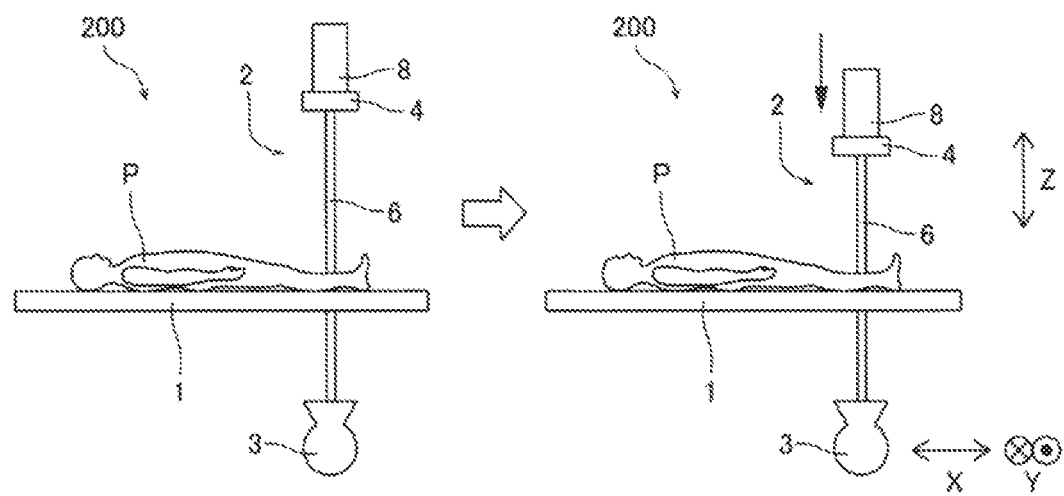
FIGS. 6A and 6B are diagrams for explaining the current image capturing range displayed on the elongate image in the X-ray image capturing device according to a second embodiment.
Figure 6B:
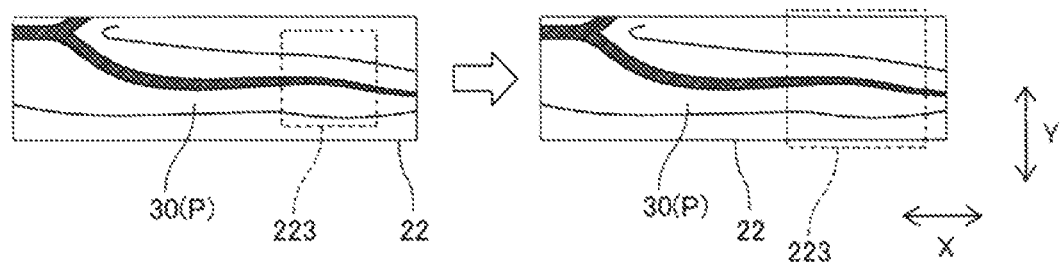

Specifically, in a state in which the current image capturing range 223 is displayed on the elongate image 22, as shown in FIG. 6A, the slide portion 8 is slid by the moving mechanism 9 to change the distance between the X-ray tube device 3 and the X-ray receiver 4. The position information acquisition unit 12 acquires the position information on the X-ray tube device 3 and the X-ray receiver 4 before and after the distance between the X-ray tube device 3 and the X-ray receiver 4 is changed. Then, as shown in FIG. 6B, the image processing unit 213 adjusts the size of the current image capturing range 223 on the elongate image 22 based on the position information acquired by the position information acquisition unit 12. In this manner, by changing the distance between the X-ray tube device 3 and the X-ray receiver 4, it is possible to enlarge or reduce the image capturing range 223 to be displayed on the elongate image 22. FIGS. 6A and 6B shows a case in which the distance between the X-ray tube device 3 and the X-ray receiver 4 is reduced. In this case, the image capturing range 223 is displayed on the elongate image 22 so that the range increases with the center position unchanged. When the distance between the X-ray tube device 3 and the X-ray receiver 4 is increased, the image capturing range 223 is displayed on the elongate image 22 so that the range decreases with the center position unchanged.

The remaining configuration of the X-ray image capturing device 200 according to the second embodiment is the same as that of the first embodiment.

(Effects of Second Embodiment)

In the second embodiment, as described above, it is configured such that the size or the shape of the image capturing range 223 to be displayed on the elongate image 22 is adjusted based on the change in the position information. With this configuration, when the size or the shape of the image capturing range 223 is changed according to the position of the top board 1 and the image capturing unit 2 and the image capturing condition of the image capturing unit on the elongate image 22, the changed image capturing range 223 can be displayed on the display unit 14. It is possible for the operator to assuredly recognize the size of the image capturing range 23 of the actually acquired X-ray image 21.

Further, in the second embodiment, as described above, the image capturing unit 2 includes an X-ray tube device 3 for irradiating the subject P with an X-ray and an X-ray receiver 4 for detecting the X-ray transmitted through the subject P, and the X-ray tube device 3 and the X-ray receiver 4 are configured so that the distance therebetween can be changed. The size of the image capturing range 223 to be displayed on the elongate image 22 can be adjusted based on the change in the position information due to the change in the distance between the X-ray tube device 3 and the X-ray receiver 4. With this configuration, it becomes possible to display an image capturing range 223 reflecting the change in the distance between the X-ray irradiation unit and the X-ray detector on the elongate image 22. As a result, the operator can easily enlarge or reduce the image capturing range 223 to be displayed on the elongate image 22 by adjusting the distance between the X-ray tube device 3 and the X-ray receiver 4 to set the image capturing range 223 to a predetermined size. Other effects of the second embodiment are the same as those of the first embodiment.

<Third Embodiment>

Next, a third embodiment of the present invention will be described with reference to FIGS. 1A and 1B, FIG. 2, FIG. 6B, and FIG. 7. In this third embodiment, an example in which the size of the image capturing range to be displayed on the elongate image 22 is adjusted based on the change in the position information due to the change in the height position of the top board 1. In the figures, note that the same reference numeral is given to a part having the same configuration as in the first and second embodiments.

The X-ray image capturing device 300 according to the third embodiment of the present invention is configured so that the size of the image capturing range 223 to be displayed on the elongate image 22 is changed by changing the height position of the top board 1 in the same manner as in the aforementioned second embodiment.

Figure 7:
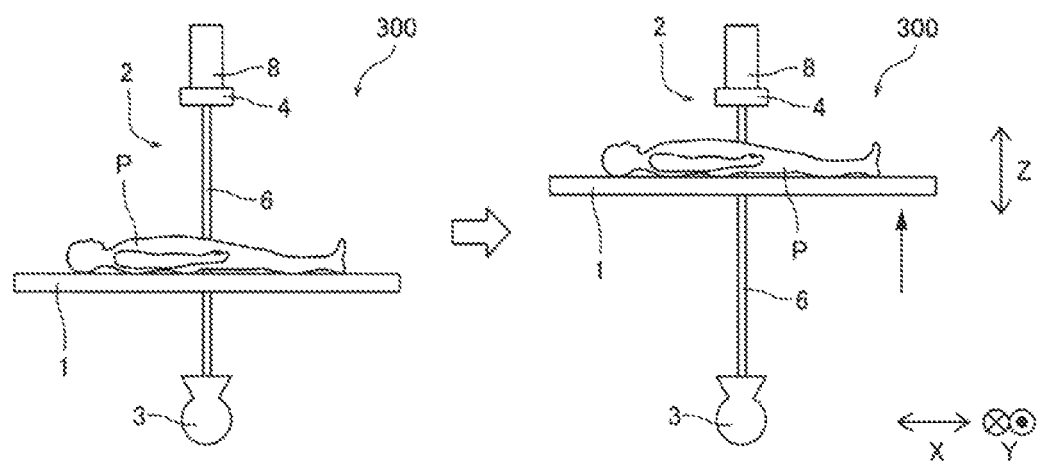
FIG. 7 is a diagram for explaining a change in a height position of a top board in the X-ray image capturing device according to a third embodiment.
Figure 9:
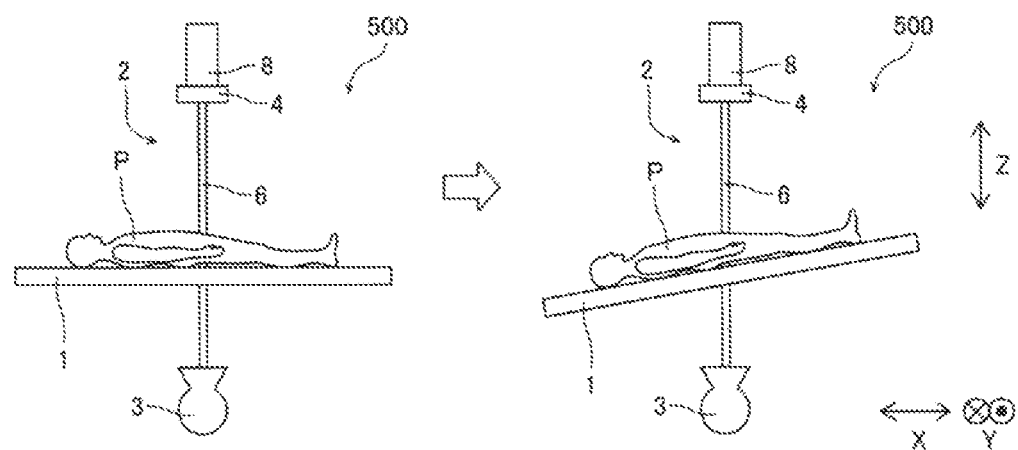
FIG. 9 is a diagram for explaining a change in an angle formed by the top board and the image capturing unit in the X-ray image capturing device according to a fifth embodiment.

Specifically, in a state in which the current image capturing range 223 is displayed on the elongate image 22, as shown in FIG. 7, the height position of the top board 1 is changed by ascending and descending the top board 1 with the moving mechanism 9. The position information acquisition unit 12 acquires the position information on the top board 1 before and after the height position of the top board 1 is changed. Then, the image processing unit 313 adjusts the size of the current image capturing range 223 on the elongate image 22 based on the position information acquired by the position information acquisition unit 12. In this manner, by changing the height position of the top board 1, it is possible to easily enlarge or reduce the image capturing range 223 to be displayed on the elongate image 22. In FIG. 9, the case in which the top board 1 is raised so as to be brought closer to the X-ray receiver 4 is shown. In this case, the image capturing range 223 is displayed on the elongate image 22 so that the range increases with the center position unchanged. When the top board 1 is lowered so as to be moved away from the X-ray receiver 4, the image capturing range 223 is displayed on the elongate image 22 so that the range decreases with the center position unchanged.

The remaining configuration of the X-ray image capturing device 300 according to the third embodiment is the same as those of the first and second embodiments.

(Effects of the Third Embodiment)

In the third embodiment, as described above, the top board 1 is configured so that the height position can be changed and the size of the image capturing range 223 to be displayed on the elongate image 22 is adjusted based on the change of the position information due to the change in the height position of the top board 1. With this configuration, it is possible to display an image capturing range 223 reflecting the change in the height position of the top board 1 on the elongate image 22. As a result, the operator can easily enlarge or reduce the image capturing range 223 to be displayed on the elongate image 22 by adjusting the height position of the top board 1 to set the image capturing range 223 to a predetermined size. Other effects of the third embodiment are the same as those of the first and second embodiments.

<Fourth Embodiment>

Next, a fourth embodiment of the present invention will be described with reference to FIGS. 1, 2 and 8. In this fourth embodiment, an example in which the shape of the image capturing range to be displayed on the elongate image 22 is adjusted based on the change in the position information due to a change of an angle formed by the top board 1 and the image capturing unit 2. In the figures, note that the same reference numeral is given to a part having the same configuration as in the first embodiment.

The X-ray image capturing device 400 according to the fourth embodiment of the present invention is configured so that the shape of the image capturing range 423 to be displayed on the elongate image 22 is changed by changing the angle formed between the top board 1 and the image capturing unit 2.

Figure 8A:
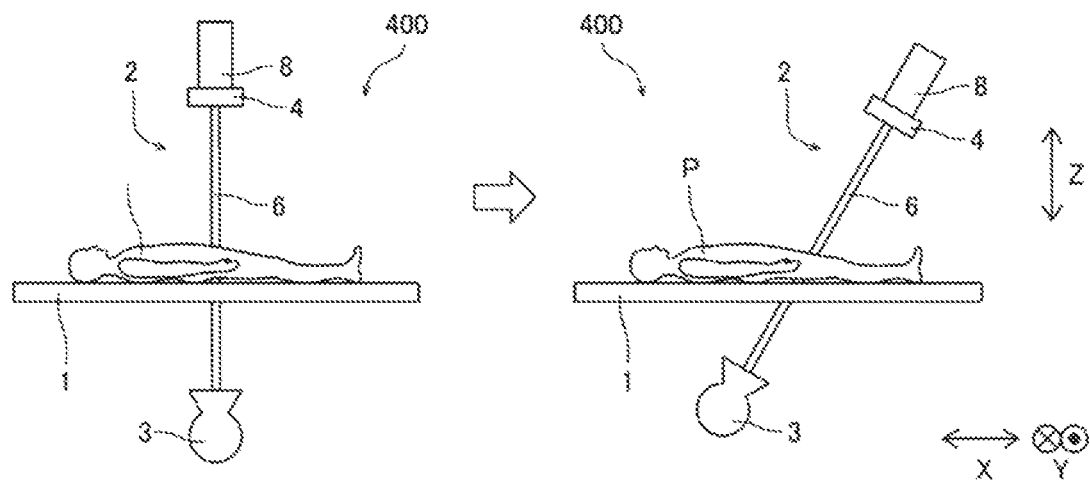
FIGS. 8A and 8B are diagrams for explaining a current image capturing range displayed on the elongate image in the X-ray image capturing device according to a fourth embodiment.
Figure 8B:
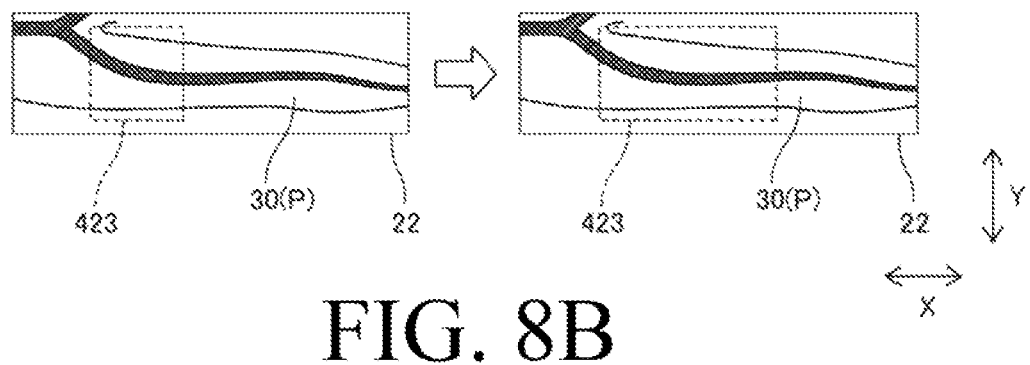

Specifically, in a state in which the current image capturing range 423 is displayed on the elongate image 22, as shown in FIG. 8A, the arm unit 6 is rotated on the plane including the X direction and the Z direction (X-Z plane) by the moving mechanism 9 to change the angle formed by the top board 1 and the image capturing unit 2. The position information acquisition unit 12 acquires the position information on the top board 1 and the image capturing unit 2 before and after the angle formed by the top board 1 and the image capturing unit 2 is changed. Then, as shown in FIG. 8B, the image processing unit 413 adjusts the shape of the current image capturing range 423 on the elongate image 22 based on the position information acquired by the position information acquisition unit 12. In the example of FIGS. 8A and 8B, the X-ray irradiation direction with respect to the top board 1 is inclined in the X-Z plane, so that the current image capturing range 423 in the elongate image 22 is in a rectangular shape. In this manner, in a state in which the angle formed by the top board 1 and the image capturing unit 2 is changed, it is possible to display the image capturing range 423 corresponding to various angles on the elongate image 22.

The remaining configurations of the X-ray image capturing device 400 according to the fourth embodiment are similar to those of the first embodiment.

(Effects of Fourth Embodiment)

In the fourth embodiment, it is configured such that the shape of the image capturing range 423 to be displayed on the elongate image 22 is adjusted based on the change in the position information as described above. This makes it possible to display the image capturing range 423 flexibly corresponding to the positions in the top board 1 and the image capturing unit 2 and the image capturing condition of the image capturing unit 2 on the elongate image 22.

In the fourth embodiment, as described above, the top board 1 and the image capturing unit 2 are configured so that the angle therebetween can be changed, and the shape of the image capturing range 423 to be displayed on the elongate image 22 is adjusted based on the change in the position information due to the change of the angle formed by the top board 1 and the image capturing unit 2. With this configuration, it is possible to display the image capturing range 423 reflecting the change in the angle formed by the top board 1 and the image capturing unit 2 on the elongate image 22. As a result, the operator can make the image capturing range 423 to be displayed so as to correspond to various angles on the elongate image 22 by adjusting the angle formed between the top board 1 and the image capturing unit 2. Other effects of the fourth embodiment are the same as those of the first, second, and third embodiments.

<Fifth Embodiment>

Next, a fifth embodiment of the present invention will be described with reference to FIGS. 1A and 1B, FIG. 2, FIG. 8B, and FIG. 9. In the fifth embodiment, an example in which the shape of the image capturing range to be displayed on the elongate image 22 is changed based on the change in the position information due to the change in the angle formed by the top board 1 and the image capturing unit 2 when the angle formed by the top board 1 and the image capturing unit 2 is changed by a method different from the fourth embodiment will be described. In the figures, note that the same reference numeral is given to a part having the same configuration as in the first and fourth embodiments.

In the same manner as in the X-ray image capturing device 400 according to the aforementioned fourth embodiment, the X-ray image capturing device 500 according to the fifth embodiment of the present invention is configured such that the shape of the image capturing range 423 to be displayed on the elongate image 22 is changed by changing the angle formed between the top board 1 and the image capturing unit 2.

Specifically, in a state in which the current image capturing range 423 is displayed on the elongate image 22, as shown in FIG. 9, the top board 1 is rotated on the plane including the X direction and in the Z direction (X-Z plane) with the moving mechanism 9 to change the angle formed by the top board 1 and the image capturing unit 2. The position information acquisition unit 12 acquires the position information on the top board 1 and the image capturing unit 2 before and after the angle formed by the top board 1 and the image capturing unit 2 is changed. Then, the image processing unit 513 adjusts the shape of the current image capturing range 423 on the elongate image 22 based on the position information acquired by the position information acquisition unit 12 as shown in FIG. 8B. In this manner, in a state in which the angle formed by the top board 1 and the image capturing unit 2 is changed, it is possible to display the image capturing range 423 corresponding to various angles on the elongate image 22.

The remaining configurations of the X-ray image capturing device 500 according to the fifth embodiment are the same as those of the first and fourth embodiments.

(Effects of Fifth Embodiment)

In the fifth embodiment, as described above, the top board 1 and the image capturing unit 2 are configured such that the angle therebetween can be changed and the shape of the image capturing range 423 to be displayed on the elongate image 22 can be adjusted based on the change in the position information due to the change in the angle formed by the top board 1 and the image capturing unit 2. With this configuration, it is possible to display the image capturing range 423 reflecting the change in the angle formed by the top board 1 and the image capturing unit 2 on the elongate image 22. As a result, the operator can make the image capturing range 423 to be displayed so as to correspond to various angles on the elongate image 22 by adjusting the angle formed between the top board 1 and the image capturing unit 2. Other effects of the fifth embodiment are the same as those of the first and fourth embodiments.

<Sixth Embodiment>

Next, a sixth embodiment of the present invention will be described with reference to FIGS. 1A and 1B, FIG. 2, and FIG. 6B. In the sixth embodiment, an example in which the size of the image capturing range to be displayed on the elongate image 22 is adjusted based on change in the X-ray radiation field of the X-ray tube device 3 will be explained.

In the figures, note that the same reference numeral is given to a part having the same configuration as in the first and second embodiments.

The X-ray image capturing device 600 according to the sixth embodiment of the present invention is configured such that the size of the image capturing range 223 to be displayed on the elongate image 22 is changed by changing the X-ray radiation field of the X-ray tube device 3.

Specifically, in a state in which the current image capturing range 223 is displayed on the elongate image 22, the X-ray radiation field of the X-ray tube device 3 is changed by controlling the collimator 7. The image processing unit 613 adjusts the size of the current image capturing range 223 on the elongate image 22 based on the control information at the time of controlling the collimator 7. For example, when the X-ray radiation field is enlarged by the collimator 7, as shown in FIG. 6B, based on the position information, the image capturing range 223 is displayed on the elongate image 22 so as to become larger. When the X-ray radiation field is reduced by the collimator 7, the image capturing range 223 is displayed on the elongate image 22 so that the image capturing range 223 becomes small. In this manner, by changing the X-ray radiation field of the X-ray tube device 3, it is possible to easily enlarge or reduce the image capturing range 223 to be displayed on the elongate image 22. Since the size of the X-ray radiation field is proportional to the area through which the X-ray penetrates the subject P, by reducing the X-ray radiation field, the X-ray exposure dose of the subject P can be reduced.

The remaining configurations of the X-ray image capturing device 600 according to the sixth embodiment are the same as those of the first and second embodiments.

(Effects of Sixth Embodiment)

In the sixth embodiment, as described above, the image capturing unit 2 is configured to include a collimator 7 capable of adjusting the X-ray radiation field which is an irradiation range of the X-ray, and the size of the image capturing range 223 to be displayed on the elongate image 22 is adjusted based on the change of the X-ray radiation field. With this configuration, it is possible to display the image capturing range 223 reflecting the change in the X-ray radiation field on the elongate image 22. As a result, the operator can easily enlarge or reduce the image capturing range 223 to be displayed on the elongate image 22 by adjusting the X-ray radiation field and also can move the top board 1 and the image capturing unit 2 to a target position. In addition, when the image capturing range 223 is reduced by adjusting the X-ray radiation field, the irradiation range of the X-ray is reduced, so that the X-ray exposure dose of the subject P can be reduced. Other effects of the sixth embodiment are the same as those of the first and second embodiments.

[Modified Embodiment]

It should be understood that the embodiments disclosed here are examples in all respects and are not restrictive. The scope of the present invention is shown by the scope of the claims rather than the descriptions of the embodiments described above, and includes all changes (modifications) within the meaning of equivalent and the scope of claims.

For example, in the first to sixth embodiments, the top board movement image capturing is performed by moving the top board 1 in the X direction and the Y direction with respect to the image capturing unit 2, but the present invention is limited to this. In the present invention, the top board movement image capturing may be performed by moving the image capturing unit 2 in the X direction and the Y direction with respect to the top board 1. Further, the top board 1 and the image capturing unit 2 may be moved only in one of the X direction and the Y direction. In addition, the top board movement image capturing may be performed by moving either the top board 1 or the image capturing unit 2 in the X direction or (and) Y direction while moving in the Z direction.

In the first to sixth embodiments, the control unit 10 is equipped with the image information acquisition unit 11, the position information acquisition unit 12, and the image processing unit 13, but the present invention is not limited thereto. In the present invention, the image information acquisition unit 11, the position information acquisition unit 12, and the image processing unit 13 may be provided separately from the control unit 10.

In the first to sixth embodiments, for the position information of the top board 1 and the image capturing unit 2 acquired by the position information acquisition unit 12, the coordinate information (X, Y, Z) is used, but the present invention is not limited. In the present invention, other coordinate systems, such as, e.g., a polar coordinate system, may be used as the position information on the top board 1 and the image capturing unit 2, but not limited to rectangular coordinate systems, such as, e.g., coordinate information (X, Y, Z).

In the fourth embodiment, when the image capturing range 423 is displayed on the elongate image 22, the arm unit 6 is rotated on the plane including the X direction and in the Z direction (X-Z plane) by the moving mechanism 9, and the angle formed by the top board 1 and the image capturing unit 2 is changed, but the present invention is not limited to this. According to the present invention, when displaying the image capturing range 423 on the elongate image 22, the arm unit 6 may be rotated on the plane including the Y direction and in the Z direction plane (Y-Z plane) by the moving mechanism 9 to change the angle formed by the top board 1 and the image capturing unit 2.

In the fifth embodiment, when the image capturing range 423 is displayed on the elongate image 22, the top board 1 is rotated on the plane including the X direction and in the Z direction (X-Z plane) by the moving mechanism 9, and the angle formed by the top board 1 and the image capturing unit 2 is changed, but the present invention is not limited to this. According to the present invention, when displaying the image capturing range 423 on the elongate image 22, the top board 1 may be rotated on the plane including the Y direction and the Z direction plane (Y-Z plane) by the moving mechanism 9 to change the angle formed by the top board 1 and the image capturing unit 2.

In the first to sixth embodiments, an example in which the lower limb portion 30 of the subject P is subjected to X-ray image capturing is shown, but the present invention is not limited thereto. In the present invention, a portion other than the lower limb portion 30 such as the arm portion and the torso portion of the subject P may be X-ray image captured. Further, in the present invention, an X-ray image capturing device for capturing a subject of an animal other than a human body may be configured.

Further, each of the second to sixth embodiments has been described as an independent embodiment, but the present invention is not limited thereto. In the present invention, any one of the second to sixth embodiments described above may be combined. For example, the second and fourth embodiments may be combined. In this case, based on the change on the distance between the X-ray tube device 3 and the X-ray receiver 4 and the change in the position information by changing the angle formed by the top board 1 and the image capturing unit 2, the size and the shape of the capturing range 223 to be displayed on the elongate image 22 are adjusted.

The invention claimed is:

1. An X-ray image capturing device comprising:
a top board configured to lay a subject thereon;
an image capturing unit configured to capture an X-ray image by irradiating the subject with an X-ray and detecting the X-ray transmitted through the subject;
an image processing unit configured to generate an elongate image which is an image longer than the X-ray image by performing joining processing of a plurality of the X-ray images; and
a display unit configured to display the elongate image and an image capturing range of the image capturing unit,
wherein the image capturing range of the image capturing unit is displayed on the elongate image based on position information of the top board and the image capturing unit.

2. The X-ray image capturing device as recited in claim 1, further comprising:
a moving mechanism capable of changing a relative position of the top board with respect to the image capturing unit; and
a position information acquisition unit configured to acquire the position information,
wherein the image capturing range is displayed on the elongate image based on a change in the position information due to a change in the relative position by the moving mechanism.

3. The X-ray image capturing device as recited in claim 1, wherein
the elongate image is generated by performing joining processing of the X-ray images based on image capturing position information which is the position information at the time of capturing the X-ray image, and
the image capturing range based on current position information is displayed on the elongate image generated based on the image capturing position information.

4. The X-ray image capturing device as recited in claim 1, wherein
a size or a shape of the image capturing range to be displayed on the elongate image is adjusted based on a change in the position information.

5. The X-ray image capturing device as recited in claim 4, wherein
the image capturing unit includes an X-ray irradiation unit configured to irradiate the subject with the X-ray and an X-ray detection unit configured to detect the X-ray transmitted through the subject,
the X-ray irradiation unit and the X-ray detection unit are configured to be changed in a distance therebetween, and
a size of the image capturing range to be displayed on the elongate image is adjusted based on the change in the position information due to a change in a distance between the X-ray irradiation unit and the X-ray detection unit.

6. The X-ray image capturing device as recited in claim 4, wherein
the top board is adjustable in a height position, and
the image capturing range to be displayed on the elongate image is adjustable in a size based on the change in the position information due to a change in the height position of the top board.

7. The X-ray image capturing device as recited in claim 4, wherein
the top board and the image capturing unit are adjustable in an angle therebetween, and
the image capturing range to be displayed on the elongate image is adjustable in shape based on the change in the position information due to a change of an angle formed by the top board and the image capturing unit.

8. The X-ray image capturing device as recited in claim 1, wherein
the image capturing unit includes an X-ray irradiation field adjusting unit capable of changing an X-ray radiation field which is an irradiation range of an X-ray, and
the image capturing range to be displayed on the elongate image is adjustable in size based on a change in the X-ray radiation field.

9. The X-ray image capturing device as recited in claim 1, wherein the X-ray image and the elongate image include an image in which a lower limb portion of the subject is image-captured.

10. An X-ray image capturing device comprising:
a top board configured to allow a subject to lay thereon;
an image capturing unit configured to capture a plurality of X-ray images by irradiating the subject with an X-ray and detecting the X-ray transmitted through the subject;
an image processing unit configured to generate an elongate image by joining the plurality of X-ray images, the elongate image being longer than individual ones of the plurality of X-ray images; and
a display unit configured to display the elongate image and an image capturing range of the image capturing unit,
wherein the image capturing range of the image capturing unit is superimposed on the elongate image, and
wherein the image capturing range is based on position information of the top board and the image capturing unit.

11. The X-ray image capturing device as recited in claim 10, further comprising:
a moving mechanism capable of changing a relative position of the top board with respect to the image capturing unit; and
a position information acquisition unit configured to acquire the position information,
wherein the image capturing range is superimposed on the elongate image based on a change in the position information due to a change in the relative position.

12. The X-ray image capturing device as recited in claim 10,
wherein the elongate image is generated by performing joining processing of the plurality of X-ray images based on image capturing position information corresponding to each of the plurality of X-ray image, and
wherein the image capturing range based on current position information is superimposed on the elongate image generated based on the image capturing position information.

13. The X-ray image capturing device as recited in claim 10, wherein a size or a shape of the image capturing range to be superimposed on the elongate image is adjusted based on a change in the position information.

14. The X-ray image capturing device as recited in claim 13,
wherein the image capturing unit includes an X-ray irradiation unit configured to irradiate the subject with the X-ray and an X-ray detection unit configured to detect the X-ray transmitted through the subject,
wherein the X-ray irradiation unit and the X-ray detection unit are configured to be changed in a distance therebetween, and
wherein a size of the image capturing range to be superimposed on the elongate image is adjusted based on the change in the position information due to a change in a distance between the X-ray irradiation unit and the X-ray detection unit.

15. The X-ray image capturing device as recited in claim 13,
wherein the top board is adjustable in a height position, and
wherein the image capturing range to be superimposed on the elongate image is adjustable in a size based on the change in the position information due to a change in the height position of the top board.

16. The X-ray image capturing device as recited in claim 13,
wherein the top board and the image capturing unit are adjustable in an angle therebetween, and
wherein the image capturing range to be superimposed on the elongate image is adjustable in shape based on the change in the position information due to a change of an angle formed by the top board and the image capturing unit.

17. The X-ray image capturing device as recited in claim 10,
wherein the image capturing unit includes an X-ray irradiation field adjusting unit capable of changing an X-ray radiation field which is an irradiation range of an X-ray, and
wherein the image capturing range to be superimposed on the elongate image is adjustable in size based on a change in the X-ray radiation field.

18. The X-ray image capturing device as recited in claim 10, wherein the position information comprises X, Y, Z coordinate information.

* * * * *